United States Patent [19] [11] 4,243,614
Gilbert [45] Jan. 6, 1981

[54] PROCESS FOR PRODUCING HEXANITROSTILBENE

[75] Inventor: Everett E. Gilbert, Morristown, N.J.

[73] Assignee: The United States of America as represented by the Secretary of the Army, Washington, D.C.

[21] Appl. No.: 69,216

[22] Filed: Aug. 23, 1979

[51] Int. Cl.³ .................................................. C07C 79/10
[52] U.S. Cl. .................................................. 568/931
[58] Field of Search .................................. 260/645, 646

[56] References Cited
U.S. PATENT DOCUMENTS
3,505,413  4/1970  Shipp .................................. 260/646
4,085,152  4/1978  Salter et al. ........................ 260/645

FOREIGN PATENT DOCUMENTS
2702463  1/1977  Fed. Rep. of Germany ........... 260/645
2256144  12/1973 France .................................. 260/645

Primary Examiner—Leland A. Sebastian
Attorney, Agent, or Firm—Nathan Edelberg; Robert P. Gibson; A. Victor Erkkila

[57] ABSTRACT 2,2',4,4',6,6'-Hexanitrostilbene is produced by reacting 2,2',4,4',6,6'-hexanitrobibenzyl with copper sulfate in hexamethylphosphoric triamide as a reaction solvent. The HNS product can be thus produced in greater than 80% yields.

10 Claims, No Drawings

PROCESS FOR PRODUCING HEXANITROSTILBENE

GOVERNMENTAL INTEREST

The invention described herein may be manufactured, used and licensed by the Government for Governmental purposes without the payment to me of any royalties thereon.

BACKGROUND OF THE INVENTION

The present invention relates to a process for preparing 2,2',4,4',6,6'-hexanitrostilbene (HNS) from 2,2',4,4',6,6'-hexanitrobibenzyl (HNBB).

HNS is a thermally stable explosive. It is also useful as a nucleating agent for promoting a desired mode of crystallization of 2,4,6-trinitrotoluene (TNT) in melt-cast TNT explosives.

HNS has been prepared by oxidation of TNT but the yields of HNS obtained thereby have been rather low. Thus, Shipp, U.S. Pat. No. 3,505,413 and NOLTR (U.S. Naval Ordnance Laboratory Technical Report) 64-34 (1964), and Shipp and Kaplan, Journal of Organic Chemistry, 31, 857 (1966), disclose a process for preparing HNS, which comprises reacting TNT with sodium hypochlorite in a solvent mixture consisting of two parts of tetrahydrofuran (THF) and one part of methanol by volume. The crude HNS is thus obtained in yields of 40–45% of theory and is purified by extraction with hot acetone to remove impurities present in substantial amounts. Shipp and Kaplan disclose that TNT can be converted to HNBB or HNS with sodium hypochlorite under various conditions, and obtained a 79% yield of HNBB from TNT. However, they did not disclose any procedure for producing HNS from HNBB.

British patent application 76/2501, Jan. 22, 1976 to Salter et al discloses a process, wherein TNT is reacted in THF-methanol solution with sodium hypochlorite at about 10°–20° C., after which an aqueous solution of an organic amine, preferably trimethylamine, is added. By this process HNS is obtained in yields of about 50% of theory.

Kompolthy et al, Hungarian Patent T/9639 VE-719 (CO6 f 9/04) disclose a process for air oxidation of TNT to produce HNS in two steps, viz.:

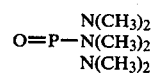  (a)

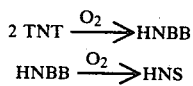  (b)

They obtained HNBB in 82% yield and HNS in yields of 76–91% from HNBB by employing dimethylformamide or dimethylsulfoxide as solvents in a reaction mixture comprising methanol, potassium hydroxide, copper sulfate and pyridine. This Kompolthy et al procedure has been repeated by other workers but yields of only 25–40% of HNS have been obtained.

BRIEF SUMMARY OF THE INVENTION

It is an object of the present invention to provide a process for the preparation of 2,2',4,4',6,6'-hexanitrostilbene (HNS) in high yields from 2,2',4,4',6,6'-hexanitrobibenzyl (HNBB).

It is a further object of the present invention to provide a process for the preparation of HNS from HNBB which does not require the use of methanol, potassium hydroxide and pyridine and other solvents essential in the Kompolthy et al process discussed above.

Other objects will become apparent from the following description of the invention.

In accordance with the process of the present invention, HNS can be produced in high yields by reacting HNBB with copper sulfate in a reaction medium consisting essentially of hexamethylphosphoric triamide (HMPT) having the following formula:

$$O=P\begin{array}{l}N(CH_3)_2\\N(CH_3)_2\\N(CH_3)_2\end{array}$$

The term copper sulfate, as used in the specification and claims, is synonomous with the terms cupric sulfate and copper (II) sulfate also employed.

In carrying out the process of the present invention the reactants are mixed with sufficient HMPT to disperse or dissolve the HNBB and provide a readily stirrable reaction mixture. The amount of HMPT solvent employed generally ranges from about 2 to 12 parts by volume, and preferably about 4 to about 10 parts by volume per part by weight of HNBB. Larger amounts of HMPT can be used effectively but are unnecessary and hence are relatively uneconomical.

The amount of copper sulfate employed can be varied widely. Theoretically, two moles of copper sulfate per mole of HNBB are required to effect the conversion of HNBB to HNS according to the following reaction:

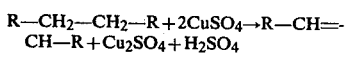

wherein R signifies the 2,4,6-trintrophenyl radical. However, by introducing a stream of an oxygen-containing gas, such as oxygen or air, into the reaction mixture, the amount of copper sulfate can be reduced much below this amount, for example, to as low as about one tenth mole of copper sulfate per mole of HNBB, and even lower, with equal or good results. Also, anhydrous and hydrated cupric sulfate can be employed with equivalent results in the present process.

The reaction can be carried out at temperatures ranging from about 30° C. to 100° C., and is preferably accomplished at temperatures between about 50° C. and 75° C. The reaction will still take place at lower temperatures but more slowly. The extent of conversion of HNBB to HNS can be generally increased by increasing the temperature and/or duration of heating of the reaction mixture. While the reaction can be carried out at temperatures above 100° C., they involve greater energy requirements and promote side reactions, and are hence less preferred.

The HNS can be recovered from the reaction mixture, for example, by diluting the reaction mixture with water to precipitate the HNS. The precipitated HNS can be separated by filtration and purified in known manner, e.g. by extraction with acetone.

The following examples illustrate specific embodiments of the method of carrying out the process of the present invention.

EXAMPLE 1

A mixture of 1.2 g. (0.0027 mole) of HNBB, 0.85 g. (0.0053 mole) of anhydrous copper (II) sulfate (CuSO$_4$), and 15 ml. of hexamethylphosphoric triamide (HMPT)

was heated into agitation for 3 hours at 70° C. The resulting mixture was poured into water and the solid which precipitated was separated by filtration and dried. The resulting solid (1.2 g.) was slurried and agitated in 50 ml of acetone at room temperature for 15 minutes, after which the slurry was filtered and the filter cake was washed with acetone and dried. 1.0 gram of HNS, mp 310° C. (dec.), was thus obtained, which corresponds to a yield of 83% of theory.

EXAMPLE 2

The procedure of example 1 was repeated except that the reaction mixture was heated for 1 hour at 55° C. The yield of HNS thus obtained was 0.5 g., corresponding to 42% of theory.

EXAMPLE 3

The procedure of example 1 was repeated except that the amount of anhydrous copper sulfate employed was reduced to 0.1 g. (0.00063 mole) and a steady stream of oxygen was bubbled into the reaction mixture at a rate of about 30 ml. per minute. The yield of HNS thus obtained was 1.0 g. corresponding to 83% of theory.

EXAMPLE 4

The procedure of example 3 was repeated but using 0.2 g. (0.00126 mole) of anhydrous copper sulfate. The yield of HNS obtained was 1.0 g., corresponding to 83% of theory.

EXAMPLE 5

The procedure of example 3 was repeated but using 0.4 g. (0.00252 mole) of anhydrous copper sulfate. The yield of HNS obtained was 1.0 g., corresponding to 83% of theory.

EXAMPLE 6

The procedure of example 3 was repeated but using only 0.05 g. (0.00031 mole) of anhydrous copper sulfate. The yield of HNS produced was 0.9 g. (75% of theory).

EXAMPLE 7

The procedure of example 3 was repeated except that the copper sulfate was omitted. All of the HNBB was recovered unchanged.

EXAMPLE 8

The procedure of example 6 was repeated except that the reaction period was 6 hours instead of 3 hours. The yield of HNS obtained was 1.0 g., corresponding to 83% of theory.

EXAMPLE 9

The procedure of example 3 was repeated except that 0.16 g. (0.00063 mole) of copper (II) sulfate pentahydrate ($CuSO_4.5H_2O$) was used, which is equivalent in amount to the anhydrous copper sulfate employed in that example. The yield of HNS thus obtained was 1.0 g. = 83% of theory.

EXAMPLE 10

The procedure of example 3 was repeated except that air was introduced at a rate of about 30 ml. per minute in place of oxygen. The yield of HNS obtained was 0.9 g., corresponding to 75% of theory.

EXAMPLE 11

The procedure of example 10 was repeated but using a reaction period of 6 hours instead of 3 hours. The yield of HNS was 0.95 g. (79% of theory).

EXAMPLE 12

A mixture of 3.6 g. (0.008 mole) of HNBB, 0.5 g. (0.002 mole) of copper (II) sulfate pentahydrate and 15 ml. of HMPT was heated and agitated at 70° C. for 3 hours, during which a steady stream of oxygen was introduced into the reaction mixture. The resulting mixture was processed in the manner described in example 1. The yield of HNS thus obtained was 0.925 g., corresponding to 77% of theory.

The use of HMPT as a solvent in the reaction of copper (II) sulfate with HNBB according to the present invention produces HNS in unexpectedly high yields. This is shown by the fact that substantially lower yields of HNS were obtained when the procedure of example 3 was repeated using equal amounts (15 ml) of other solvents, as follows:

| Solvent | Yield of HNS, % Theory |
| --- | --- |
| N,N-dimethylformamide | 54 |
| N-methylpyrrolidinone | 38 |
| dimethyl sulfoxide | 54 |
| pyridine | 58 |
| Tetramethylurea | 8 |
| HMPT | 83 |

Also, the use of copper (II) sulfate in conjunction with HMPT solvent according to the process of the present invention is advantageous, as shown by the fact that when the procedure of example 3 was repeated using other copper and cobalt salts in equivalent amounts, considerably inferior yields of HNS were obtained, as follows:

| Salt | Yield of HNS, % Theory |
| --- | --- |
| $CuBr_2$ | 33 |
| $Cu(OOCCH_3)_2 . H_2O$ | 58 |
| *$CuCl_2$ | 46 |
| $CoCl_2 . 6H_2O$ | 33 |
| $Co(OOCCH_3)_2 . 4H_2O$ | 33 |
| Co-ethylenediamine-2,4-pentanedione complex | 33 |
| $CuSO_4$ | 83 |

*0.0075 mole $CuCl_2$ was used instead of 0.0053 mole of $CuSO_4$ in the procedure of example 1, which gave a 83% yield of HNS.

In my copending U.S. Patent application Ser. No. 020,881, filed Mar. 15, 1979, I have disclosed and claimed a process for producing HNS be reacting HNBB with a copper ammino compound, e.g. copper tetramminosulfate, in a solvent, including hexamethylphosphoramide, also known as hexamethylphosphoric triamide (HMPT). The present application does not include the use of HMPT in conjunction with copper amminosulfate as claimed in said application.

The foregoing disclosure is merely illustrative of the principles of this invention and is not to be interpreted in a limiting sense. I wish it to be understood that I do not desire to be limited to the exact details of construction shown and described because obvious modifications will occur to a person skilled in the art.

I claim:

1. A process for producing 2,2',4,4',6,6'-hexanitrostilbene, which comprises reacting 2,2',4,4',6,6'-hexanitrobibenzyl with copper sulfate in a solvent consisting essentially of hexamethylphosphoric triamide.

2. The process of claim 1, wherein the amount of hexamethylphosphoric triamide ranges from about 2 to 12 parts by volume per part by weight of 2,2',4,4',6,6'-hexanitrobibenzyl.

3. The process of claim 1, wherein the reaction is carried out at a temperature within the range of about from 30° C. to 100° C.

4. The process of claim 1, wherein a stream of an oxygen-containing gas is introduced into the reaction mixture.

5. The process of claim 4, wherein the amount of copper sulfate is less than 2 moles per mole of 2,2',4,4',6,6'-hexanitrobibenzyl.

6. The process of claim 4 wherein the oxygen-containing gas is oxygen.

7. The process of claim 4, wherein the oxygen-containing gas is air.

8. The process of claim 4, wherein the reaction is carried out at a temperature within the range of about from 30° C. to 100° C.

9. The process of claim 1, wherein the copper sulfate is anhydrous copper sulfate.

10. The process of claim 1, wherein the copper sulfate is copper sulfate pentahydrate.

* * * * *